(12) United States Patent
Crockatt et al.

(10) Patent No.: US 10,100,025 B2
(45) Date of Patent: Oct. 16, 2018

(54) PRODUCTION OF FURANS

(71) Applicant: NEDERLANDSE ORGANISATIE VOOR TOEGEPAST-NATUURWETENSCHAPPELIJK ONDERZOEK TNO, s'Gravenhage (NL)

(72) Inventors: Marc Crockatt, 's-Gravenhage (NL); Jan Harm Urbanus, 's-Gravenhage (NL); Johannes Wouterus Van Groenestijn, 's-Gravenhage (NL); Martijn Constantijn De Koning, 's-Gravenhage (NL)

(73) Assignee: NEDERLANDSE ORGANISATIE VOOR TOEGEPAST-NATUUREWETENSCHAPPELIJK ONDERZOEK TNO, 'S-Gravenhage (NL)

( * ) Notice: Subject to any disclaimer, the term of this patent is extended or adjusted under 35 U.S.C. 154(b) by 0 days.

(21) Appl. No.: 15/526,022

(22) PCT Filed: Nov. 20, 2015

(86) PCT No.: PCT/NL2015/050816
§ 371 (c)(1),
(2) Date: May 11, 2017

(87) PCT Pub. No.: WO2016/080839
PCT Pub. Date: May 26, 2016

(65) Prior Publication Data
US 2017/0320843 A1   Nov. 9, 2017

(30) Foreign Application Priority Data
Nov. 20, 2014   (EP) .................................... 14194062

(51) Int. Cl.
*C07D 307/36* (2006.01)
(52) U.S. Cl.
CPC .................................. *C07D 307/36* (2013.01)
(58) Field of Classification Search
CPC .................................................... C07D 307/36
See application file for complete search history.

(56) References Cited

U.S. PATENT DOCUMENTS 4,939,277 A   7/1990   Imaki et al.

FOREIGN PATENT DOCUMENTS

WO   03042200 A1   5/2003

OTHER PUBLICATIONS

International Search Report and Written Opinion for International Application No. PCT/NL2015/050816 (dated Mar. 1, 2016) (8 Pages).

*Primary Examiner* — Timothy R Rozof
(74) *Attorney, Agent, or Firm* — Lucas & Mercanti LLP

(57) ABSTRACT

The invention relates to obtaining furans from biomass. In particular, the invention relates to obtaining furans from polyols, such as tetrahydroxybutane. In accordance with the invention tetrahydroxybutane is converted to furan in the presence of a catalyst. The tetrahydroxybutane may be dissolved in a solvent such as water.

23 Claims, No Drawings

PRODUCTION OF FURANS

CROSS-REFERENCE TO RELATED APPLICATIONS

This application is a 371 of PCT/NL2015/050816, filed Nov. 20, 2015, which claims the benefit of European Patent Application No. 14194062.7, filed Nov. 20, 2014.

FIELD OF THE INVENTION

The invention relates to obtaining furans from biomass. In particular, the invention relates to obtaining furans from polyols, such as tetrahydroxybutane.

BACKGROUND OF THE INVENTION

Furan is an important base chemical. It serves e.g. as a building block in the production of several specialty chemicals. A current process for the production of furan is a heavy metal (e.g. copper) catalyzed oxidation of 1,3-butadiene. 1,3-Butadiene is obtained from fossil feedstock such as natural oil and gas. Due to the depletion of the fossil feedstock, alternative sources and methods for the production of furan are desired.

Biomass is considered to advantageously lack many of the drawbacks of fossil feedstock. It is renewable, its use does not increase the $CO_2$-levels in the atmosphere, and processing of biomass is less harmful to the environment. Biomass may be obtained as dead trees, yard clippings, wood chips, plant residues or even municipal solid waste and the like. Alternatively, biomass is actively produced as corn, sugarcane, bamboo and the like or as a variety of tree species such as oil palm (palm oil).

A major component of biomass is polymeric sugar such as starch, cellulose and hemi-cellulose. By processing biomass, sugars such as glucose and xylose, as well as sugar derivatives such as erythritol, can be obtained.

Erythritol is a 1,2,3,4-tetrahydroxybutane. Apart from erythritol, there are two more isomers of 1,2,3,4-tetrahydroxybutane: D-threitol and L-threitol. In the context of the present invention these three isomers will be referred to as tetrahydroxybutane. These compounds have structures according to the following formulae:

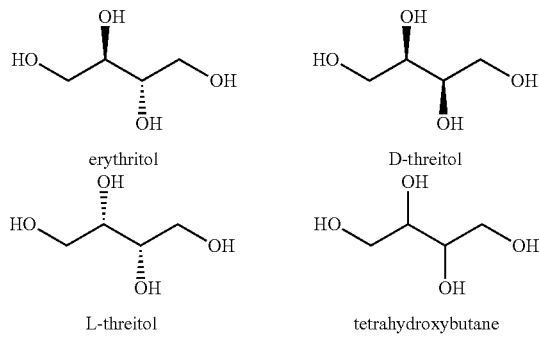

SUMMARY OF THE INVENTION

A current process for the preparation of furan, aiming to take advantage of the favorable properties of biomass, is the decarbonylation of furfural. Furfural can be obtained from e.g. xylose which is obtainable from biomass. Hence, a two-step process is required. The present invention is directed to the preparation of furan directly from a sugar derivative which is obtainable from biomass, thus no intermediate step or compound is required. Hence, the present invention is directed to a reaction according to the following scheme:

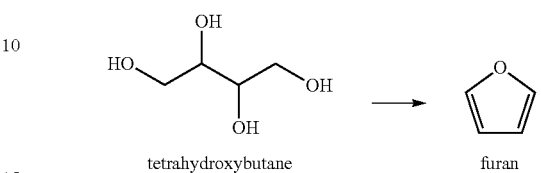

Such a process is highly advantageous since it allows for less process steps and a higher atom-efficiency. Atom-efficiency expresses the efficiency with which atoms from the starting material are incorporated into the final product. The higher the atom-efficiency of a reaction, the less waste typically results from that reaction. In a process wherein xylose ($C_5H_{10}O_5$) is the starting material for furan ($C_4H_4O$), $CH_6O_4$ is rejected throughout the processes as waste in the form of carbon monoxide (CO) and water ($3 \times H_2O$). However, in a process wherein the tetrahydroxybutane ($C_4H_{10}O_4$) is the starting material for furan, only three water molecules ($3 \times H_2O$) are rejected as waste. When dealing with small molecular weights, as is the case for the present invention, this results in a significant improvement in atom-efficiency, which may be more than 34% in accordance with the present invention.

An additional advantage of the present invention is that no toxic CO is emitted, as is generally the case in the process of decarbonylation of furfural. Required safety measures for the present invention may therefore be less strict.

WO-A-03/042200 discloses the use of erythritol as starting material for the synthesis of tetrahydrofuran (THF) under hydrogenation conditions in the presence of a rhenium catalyst. Furan is an intermediate in this process and is accidentally obtained only as a minor side product.

U.S. Pat. No. 4,939,277 discloses the reaction of erythritol to cis-3,4-dimethoxytetrahydrofuran under acidic conditions. No furan is obtained.

The present invention does not require hydrogenation conditions. It neither requires presence of a rhenium catalyst or any other heavy metals. For these reasons, the present invention is environmentally more benign and operationally more simple.

DETAILED DESCRIPTION OF THE INVENTION

The present invention is thus directed to a method to obtain furan comprising providing the tetrahydroxybutane and converting the tetrahydroxybutane to furan in the presence of a catalyst, wherein the tetrahydroxybutane is heated in the presence of the catalyst to a temperature of at least 130° C. Preferably this conversion is carried out in a single step.

The environmental friendliness is a major advantage of the present invention, i.e. the present invention is particularly green. No heavy metals, toxic solvents or explosive gasses are required. In a preferred embodiment of the present invention, the tetrahydroxybutane is dissolved in a solvent. Preferably the solvent is a green solvent, viz. a solvent that is known to be environmentally friendly. Green solvents are for instance water, acetone, methyl ethyl ketone, ethyl acetate, isopropyl acetate, and $C_1$-$C_4$ alcohols such as ethanol, methanol, propanols and butanols. Organic solvent such as diethyl ether, dichloromethane and dioxane are not considered to be green solvents and are therefore less preferred.

For efficient conversions of the tetrahydroxybutane to furan, polar solvents, in particular polar protic solvents, are preferred. Most preferably, water is used as the solvent. Water is additionally advantageous because many components from biomass dissolve readily in water or already contain amounts of water.

Examples of polar solvents are dimethyl sulfoxide (DMSO), N-methylpyrrolidone (NMP) and dimethyl formaldehyde (DMF). These are also suitable for the present invention, however, these solvents are currently less preferred as they are currently not considered to be green. In a particular embodiment of the present invention, two or more solvents may be combined and used as such.

Preferred concentrations of the tetrahydroxybutane in the solvent are 1 to 1500 g/L, preferably, 2 to 500 g/L, more preferably 4 to 200 g/L, most preferably about 10 g/L. This concentration may be kept constant by constantly feeding tetrahydroxybutane to the process in the case of a continuous process. Alternatively, in the case of e.g. a batch process, the concentration may be an initial concentration of the tetrahydroxybutane i.e. the concentration at the start of the conversion of the tetrahydroxybutane to furan.

For the tetrahydroxybutane to be converted to furan, a dehydration reaction is required. This reaction can typically be catalyzed by an acid or a base. Hence, for the present invention the catalyst is typically an acid or a base, preferably a Brønsted acid. Anhydrides may also be suitable as catalyst. The inventors found that simple mineral acids, such as sulfuric acid and/or phosphoric acid, can effectively catalyze the conversion of the tetrahydroxybutane to furan. Optionally, the catalyst is immobilized on a solid support such as silica, aluminate, zirconia, zeolite, carbon, polymer or the like.

Preferred catalysts are selected from the group consisting of sulfuric acid, phosphoric acid, hydrochloric acid, hydrobromic acid, hydroiodic acid, acetic acid, formic acid, propylphosphonic anhydride, and combinations thereof.

In case the catalyst is an acid, the acidity of the catalyst was found to be of considerable importance. The catalyst preferably has a pKa of less than 4, more preferably less than 2, for instance from 0.5 to 1.5.

The catalyst is preferably present in an amount of 1-25 wt %, preferably 3-20 wt %, most preferably about 15 wt %. The amount of catalyst is expressed in wt % of reaction mixture at the start of the process. The reaction mixture consists essentially of the starting materials, the catalyst and the optional solvent.

Without heating the tetrahydroxybutane the conversion to furan is relatively slow. Therefore, in accordance with the present invention the tetrahydroxybutane is preferably heated in the presence of the catalyst to a temperature of at least 150° C., preferably between 150 and 300° C., even more preferably between 150 and 250° C., even more preferably between 175 and 225° C., most preferably to about 220° C.

Heating can be realized by external stimulation with a variety of heat sources. It was found that heating by microwave irradiation was particularly advantageous.

The heating of tetrahydroxybutane is typically maintained for a specific time period. Typically, the tetrahydroxybutane is heated in the presence of the catalyst for a period that depends on the type of heating. When microwave irradiation is used, heating is typically performed for a period of 1 to 60 minutes, preferably 5 to 30 minutes, more preferably between 10 and 20 minutes, most preferably about 16 minutes.

When heating by thermal heating (viz. electric heating, heating by gas flame, and the like), the time period may be different, in particular longer time periods may be required compared to when heating by microwave irradiation.

By heating the tetrahydroxybutane in a closed system to certain temperatures, pressure may increase. This may in particular occur when a solvent is present. The pressure may be controlled by a variety of methods. For instance, the size of the closed system may be varied or a valve may be present to regulate the escaping of gas. Alternatively, a gas may be introduced to increase the pressure. It was found that the conversion is preferably performed at a pressure, typically at 0 to 200 bar. Preferably the pressure is 5 to 50 bar, more preferably 10 to 30 bar, most preferably about 20 bar.

In particular embodiments, the furan is selectively evaporated. Furan has a relatively low boiling point of about 31° C., while for instance erythritol has a boiling point of about 330° C. Reaction intermediates will most likely have boiling points in between those of furan and the tetrahydroxybutane. These differences in boiling point allow for a selective evaporation, i.e. distillation of the furan during the conversion of the tetrahydroxybutane to furan. Advantageously, because of this selective evaporation, furan may be directly obtained as a major component. Furthermore, the conversion of the tetrahydroxybutane to furan may also be facilitated by the selective evaporation of the furan. This may result in a more efficient conversion.

Without wishing to be bound by theory, the inventors believe that the reaction equilibrium may be pulled to the side of the furan. For instance through a continuous process in which the furan is selectively removed once it is formed, e.g. through pervaporation or distillation procedures. Moreover, the residence time of the furan in the reaction, i.e. the time that the furan is in contact with the catalyst under reaction conditions, such as high temperatures, may be reduced. This may prevent decomposition and, as such, increase conversion efficiency.

A high conversion is advantageous for the ease of isolation of the furan. When the conversion is relatively low, e.g. 1-2 mol %, isolation is more cumbersome than when the conversion is relatively high. Therefore, the tetrahydroxybutane is preferably converted to furan in a conversion of at least 5 mol %, preferably at least 15 mol %, more preferably at least 30 mol %.

Isolation of the furan may be effected by distillation. Distillation may be performed during the reaction process or it may be performed at the end of the reaction process. For an efficient isolation of the furan, a high concentration of the furan in the solvent is advantageous. This is particularly the case if the distillation is performed at the end of the reaction process. Therefore, in a preferred embodiment, the final concentration of the furan is at least 100 µg/L, preferably at least 500 µg/L, more preferably at least 900 µg/L.

In the context of this invention, mol % means molecular percentage. As such, conversion is expressed as the percentage starting materials molecules that are converted to product molecules.

For the purpose of clarity and a concise description, features are described herein as part of the same or separate embodiments. However, it will be appreciated that the scope of the invention may include embodiments having combinations of all or some of the features described.

The invention is further illustrated by the following experimental examples.

Example 1

Preparation

Reaction mixtures were prepared according to the following procedure.

Solutions of sulfuric acid ($H_2SO_4$) in water were prepared to obtain 1 wt. %, 3 wt. % and 15 wt. % aqueous $H_2SO_4$ solutions.

500 mL duran bottles were charged with either 5, 50 or 725 gram of erythritol and a 1 wt. %, 3 wt. % or 15 wt. % $H_2SO_4$ solution such that a total volume of 500 mL was obtained. The bottle was placed in an ultrasonic bath, connected to a vacuum pump and evacuated during 15 min while the ultrasonic batch was turned on. Next, the headspace of the bottle was flushed with nitrogen and the cap of the bottle was replaced by a septum.

Reaction

In an anaerobic glovebox, a reaction vessel was charged with 10 mL of the prepared reaction mixture and sealed with a septum. The reaction vessel was loaded in a microwave (Monowave 300 from Anton Paar GmbH, Austria). The desired temperature and reaction time were programmed in the microwave according to Table 1 and the reaction was started.

Sample Preparation and Analysis

After completion of the programmed reaction time, the reaction vessel was removed from the microwave, cooled and the gas in the headspace of the reaction vessel was transferred to a headspace vial for analysis. The furan concentration in both the liquid and the gas resulting from the reaction was determined by a gas chromatography/mass spectroscopy apparatus (GC-MS) using standard techniques.

Gas chromatography was performed on a HP6890 with a Factorfour VF-1301 column of 30 m*0.25 mm, df. 1 μm, with helium as the carrier gas using an optimized temperature program.

Mass spectroscopy was performed on a Agilent 5973N MSD, with an EI ionization modus and mass detection range of 25-550 m/z.

The liquid resulting from the reaction was prepared for GS-MS analysis by extracting 1 mL reaction mixture with 1 mL dichloromethane or ethyl acetate and injecting the organic layer in the GS-MS.

Results

Results of the experiments are shown in Table 1.

TABLE 1

| Sample | erythritol (g/L) | $H_2SO_4$ (wt. %) | Temp (° C.) | Time (min) | Concentration furan in Headspace (mg/L) | Concentration furan in Liquid (mg/L) | Conversion. (%) |
|---|---|---|---|---|---|---|---|
| 1 | 10 | 1 | 220 | 16 | 2 | 201 | 3.6 |
| 2 | 10 | 1 | 180 | 16 | 0.1 | 14 | 0.25 |
| 3 | 10 | 1 | 220 | 4 | 1.1 | 106 | 1.9 |
| 4 | 1450 | 1 | 180 | 4 | 0.04 | 4 | 0 |
| 5 | 1450 | 1 | 220 | 16 | 5.2 | 515 | 0.06 |
| 6 | 10 | 3 | 180 | 16 | 0.6 | 57 | 1.0 |
| 7 | 10 | 3 | 220 | 4 | 2.2 | 223 | 4.0 |
| 8 | 10 | 3 | 180 | 4 | 0.2 | 22 | 0.39 |
| 9 | 10 | 15 | 220 | 16 | 9.5 | 951 | 17 |
| 10 | 10 | 15 | 180 | 16 | 1.7 | 169 | 3.0 |
| 11 | 10 | 15 | 220 | 4 | 5 | 498 | 8.9 |
| 12 | 10 | 15 | 180 | 4 | 1.2 | 116 | 2.1 |
| 13 | 100 | 3 | 220 | 16 | 16.3 | 1630 | 2.9 |
| 14 | 100 | 3 | 220 | 4 | 11.8 | 1184 | 2.1 |
| 15 | 100 | 3 | 180 | 16 | 2.7 | 274 | 0.49 |
| 16 | 100 | 3 | 180 | 4 | 1.1 | 115 | 0.21 |

Example 2

Example 1 was repeated using different acids than $H_2SO_4$. The use of hydroiodic acid (HI), phosphoric acid ($H_3PO_4$) and hydrochloric acid produced similar results as in Example 1.

From the results of Examples 1 and 2 it may be derived that furan may be obtained using different concentrations of erythritol, different acids and acid concentrations at various temperatures for various reaction times.

The invention claimed is:

1. Method for obtaining furan comprising providing tetrahydroxybutane and converting said tetrahydroxybutane to furan in the presence of a catalyst, wherein the tetrahydroxybutane is heated in the presence of the catalyst to a temperature of at least 130° C., wherein said catalyst is not a heavy metal catalyst.

2. Method according to claim 1, wherein the tetrahydroxybutane is dissolved in water.

3. Method according to claim 1, wherein the tetrahydroxybutane is heated in the presence of the catalyst to a temperature of at least 150° C.

4. Method according to claim 1, wherein the tetrahydroxybutane is heated in the presence of the catalyst for 1 to 60 minutes.

5. Method according to claim 1, wherein the catalyst is an acid, a base, or an anhydride.

6. Method according to claim 1, wherein the catalyst is selected from the group consisting of sulfuric acid, phosphoric acid, hydrochloric acid, hydrobromic acid, hydroiodic acid, acetic acid, formic acid, propylphosphonic anhydride, and combinations thereof.

7. Method according to claim 1, wherein the tetrahydroxybutane concentration is 1 to 1450 g/L.

8. Method according to claim 1, wherein the tetrahydroxybutane is heated by microwave irradiation.

9. Method according to claim 1, wherein the tetrahydroxybutane is converted to furan at a pressure of 0 to 200 bar.

10. Method according to claim 1, wherein furan is selectively evaporated from the reaction mixture.

11. Method according to claim 1, wherein the tetrahydroxybutane is converted to furan in a conversion of at least 5 mol %.

12. Method according to claim 1, wherein the tetrahydroxybutane is heated in the presence of the catalyst to a temperature between 150 and 300° C.

13. Method according to claim 1, wherein the tetrahydroxybutane is heated in the presence of the catalyst to a temperature between 150 and 250° C.

14. Method according to claim 1, wherein the tetrahydroxybutane is heated in the presence of the catalyst to a temperature between 175 and 225° C.

15. Method according to claim 1, wherein the tetrahydroxybutane is heated in the presence of the catalyst to a temperature of about 220° C.

16. Method according to claim 1, wherein the tetrahydroxybutane is heated in the presence of the catalyst for 10 and 20 minutes.

17. Method according to claim 1, wherein the tetrahydroxybutane is heated in the presence of the catalyst for about 16 minutes.

18. Method according to claim 5, wherein the acid is a Brønsted acid.

19. Method according to claim 18, wherein the Brønsted acid has a $pK_a$ of less than 4.

20. Method according to claim 18, wherein the Brønsted acid is immobilized on a solid support.

21. Method according to claim 1, wherein the tetrahydroxybutane concentration is about 10 g/L.

22. Method according to claim 1, wherein the tetrahydroxybutane is converted to furan at a pressure of about 20 bar.

23. Method according to claim 1, wherein the tetrahydroxybutane is converted to furan in a conversion of at least 30 mol %.

* * * * *